United States Patent
Dohi et al.

(10) Patent No.: US 6,255,549 B1
(45) Date of Patent: Jul. 3, 2001

(54) METHOD FOR PRODUCING LOW BROMINE NUMBER FRACTION

(75) Inventors: Hideyuki Dohi; Shozo Hayashi, both of Yokohama (JP)

(73) Assignee: Nippon Petrochemicals Company, Limited, Tokyo (JP)

( * ) Notice: Subject to any disclaimer, the term of this patent is extended or adjusted under 35 U.S.C. 154(b) by 0 days.

(21) Appl. No.: 09/529,749

(22) PCT Filed: Aug. 25, 1999

(86) PCT No.: PCT/JP99/04586

§ 371 Date: Apr. 19, 2000

§ 102(e) Date: Apr. 19, 2000

(87) PCT Pub. No.: WO00/10946

PCT Pub. Date: Mar. 2, 2000

(30) Foreign Application Priority Data

Aug. 25, 1998 (JP) .................................................. 10-254613

(51) Int. Cl.[7] .............................. C07C 2/54; C07C 13/28; C07C 2/64

(52) U.S. Cl. ........................ 585/447; 585/422; 585/455; 585/456

(58) Field of Search ..................................... 585/447, 455, 585/456, 422

(56) References Cited

U.S. PATENT DOCUMENTS

| 4,144,279 | 3/1979 | Sato et al. ......................... 260/668 R |
| 5,866,733 | 2/1999 | Gehrer et al. ........................... 585/25 |

FOREIGN PATENT DOCUMENTS

| 53-135959 | 11/1978 | (JP) . |
| 60-208398 | 10/1985 | (JP) . |
| 62-042938 | 2/1987 | (JP) . |
| 9-104645 | 4/1997 | (JP) . |

*Primary Examiner*—Marian C. Knode
*Assistant Examiner*—Thuan D. Dang
(74) *Attorney, Agent, or Firm*—Hollander Law Firm, P.L.C.

(57) ABSTRACT

A fraction of low bromine number mainly containing a styrenic compound/aromatic compound adduct can be attained, by feeding reaction materials of a styrenic compound and an aromatic compound to a fixed-bed flow reactor packed with a solid acid catalyst in a liquid phase at a temperature in the range of 40 to 350° C. to form a styrenic compound/aromatic compound adduct, in which (1) the feed of reaction materials is stopped when the bromine number of the above fraction is increased up to a predetermined value, (2) a saturated aromatic hydrocarbon having a mean value of the proportion of aromatic ring carbons in a molecule of 55% or more is fed to the reactor in a liquid phase at a temperature higher by 5 to 150° C. than that of the reaction mixture just before the above stopping, and (3) the feed of reaction materials is then restarted to obtain the fraction.

5 Claims, No Drawings

METHOD FOR PRODUCING LOW BROMINE NUMBER FRACTION

DESCRIPTION

1. Technical Field

This invention relates to a method for producing low bromine number fraction mainly containing styrenic compound/aromatic compound adduct that is obtained by adding a styrenic compound to an aromatic compound.

2. Background Art

The styrene/alkylbenzene adduct is used as solvents for carbonless copy paper or for other purposes such as electrically insulating oil. The method for preparing a styrene/alkylbenzene adduct by adding styrene to alkylbenzene in the presence of a solid acid catalyst in a liquid phase, is proposed in U.S. Pat. No. 4,144,279; Japanese Laid-Open Patent Publication No. S55-24145 and U.S. Pat. No. 4,289,918.

According to experiments carried out by the inventors of the present application, when the addition reaction of styrene compound to alkylbenzene in the presence of a solid acid catalyst in a liquid phase was continued for a long period of time, it was observed that the bromine number of reaction product containing the adduct besides styrene compound increases. In this process, even when the bromine number was varied, the degree of conversion itself of styrene compound did not change largely almost on the same level. It is natural to consider that the reason for the increase in bromine number exists in the change in catalytic activity and the reaction among styrene molecules, rather than in the deterioration of catalyst.

The styrene/alkylbenzene adduct itself is a compound having no unsaturated double bond, however, the fact that the bromine number (JIS K 2605) of a fraction mainly containing this compound is high means that the content of unsaturated double bonds in reaction product is large. The double bonds are liable to cause oxidation and deterioration, so that the use of reaction product as a solvent is not desirable and it is wanted to find out to cope with this problem.

DISCLOSURE OF INVENTION

A first aspect of the present invention relates to a method for producing a fraction of low bromine number, which mainly contains a styrenic compound/aromatic compound adduct, by feeding reaction materials of a styrenic compound and an aromatic compound having at least one hydrogen atom directly connected to the carbon atom of aromatic ring, to a fixed-bed flow reactor packed with a solid acid catalyst in a liquid phase at a temperature in the range of 40 to 350° C. to form a styrenic compound/aromatic compound adduct and obtaining a fraction mainly containing the above adduct by distillation, wherein the feed of reaction materials is stopped when the bromine number of the above fraction is increased up to a predetermined value relative to an initial value, after that, in place of the reaction materials, a saturated aromatic hydrocarbon having a mean value of the proportion of aromatic ring carbons relative to total carbons in a molecule of 55% or more is fed to the reactor in a liquid phase at a temperature higher by 5 to 150° C. than that of the reaction mixture just before the above stopping of feed of reaction materials, and then the feed of reaction materials is restarted to carry out the foregoing reaction so as to obtain a fraction of low bromine number.

A second aspect of the present invention relates to the method of producing a low bromine number fraction as described in the first aspect of the invention, in which the aromatic compound is benzene, toluene, xylene, ethylbenzene, cumene or a mixture of them.

A third aspect of the present invention relates to the method of producing a low bromine number fraction as described in the first and second aspect of the invention, in which the styrenic compound is styrene, α-methylstyrene or p-methylstyrene.

In accordance with the method of the present invention, it is possible to produce a fraction of low bromine number with a convenient method to use saturated aromatic compounds.

In the following, the present invention will be described in more detail.

In the aromatic compound as a raw material for the present invention, at least one hydrogen atom is connected to the carbon atom of non-condensed or condensed benzene ring. More particularly, it is exemplified by alkylbenzenes such as benzene, toluene, xylene, ethylbenzene, cumene, trimethylbenzene, ethyltoluene, diethylbenzene and butylbenzene; naphthalenes such as naphthalene and methylnaphthalene; biphenyls such as biphenyl and methyl-biphenyl; diarylalkanes such as diphenylmethane and diphenylethane; phenols such as phenol and cresol; and their mixtures.

The styrenic compound used as another kind of raw material in the present invention is exemplified by styrene, α-methylstyrene or p-methylstyrene. The method of the present invention is effective in addition reaction using a styrenic compound, however, it is not effective in the similar reaction using a halogenated compound or alcohol.

The addition reaction of styrenic compound and the above aromatic compound must be done in a liquid phase in the range of 40 to 350° C. In other words, the reaction in a vapor phase or at a temperature below 40° C. or above 350° C. is not effective because the effect to reduce the bromine number cannot be attained, and it rather contaminates reaction system, undesirably.

The pressure of reaction may be a value sufficient to maintain the reaction phase in a liquid state. In general, it can be selected from the range of 0.1 to 10 MPa. The value of WHSV (mass flow rate/mass of filled catalyst) is selected from the range of 0.1 to 500 $h^{-1}$.

As the reactor, a flow type one having a fixed bed of solid acid catalyst can be used. It is possible to provide it with an optional heating device such as an apparatus to circulate a heating medium. The reactor may be any of single tube reactor and multi-tube reactor.

After reaction, a fraction that contains main component of styrenic compound/aromatic compound adduct is obtained by the distillation of reaction mixture taken out from the reaction system. For example, when o-xylene is added to styrene, a fraction mainly containing styrene/o-xylene adduct can be obtained. The distillation to obtain the above fraction may be any of industrially adopted methods. The specific distillation such as rectification is not desirable because it causes the increase in production cost.

As described above, the bromine number of the fraction mainly containing styrenic compound/aromatic compound adduct increases with the progress of reaction.

In the present invention, the bromine number of the above fraction is measured and the reaction is once stopped when the bromine number of the reaction mixture is increased up to a predetermined value as compared with its initial value. The upper limit of the bromine number can be determined in accordance with several conditions such as the kind of catalyst, the bromine number required of intended product, and so forth. However, when the bromine number exceeds 3 g/100 g, it is difficult to reduce the bromine number even when the method of the present invention is employed. Therefore, it is necessary to carry out the series of treatment by stopping the reaction before the bromine number increases up to 3 g/100 g.

In other words, when the bromine number is increased, the feed of raw materials is once stopped and, after that, a saturated aromatic hydrocarbon is fed to the reactor in place of the raw materials, and they are passed through the reactor and brought into contact with a solid acid catalyst. By the way, it is possible to operate the reaction as if it looks like continued, by carrying out continuously the first stage reaction and the feed of saturated aromatic hydrocarbon. In other words, the reaction between the above aromatic compound and styrene are cause to proceed to some extent, meanwhile the saturated aromatic hydrocarbon is fed, so that the once increased bromine number is reduced.

In one molecule of saturated aromatic hydrocarbon herein used, the proportion of the carbon atom number of aromatic ring relative to the total carbon atom number is 55% or more and it does not have ethylenically unsaturated double bonds. More particularly, it is exemplified by alkylbenzenes such as benzene, toluene, xylene, ethylbenzene, cumene, trimethylbenzene, ethyltoluene, diethylbenzene and butylbenzene; naphthalenes such as naphthalene and methylnaphthalene; biphenyls such as biphenyl and methylbiphenyl; diarylalkanes such as diphenylmethane and diphenylethane and a mixture of them.

Triethylbenzene and hexylbenzene are alkylbenzenes. However, the proportion of aromatic carbons in the molecules is 50% (i.e., number of aromatic carbons/total carbon number=$6/12$=0.5), therefore, they are not suitable as saturated aromatic hydrocarbons used for the present invention.

Incidentally, it is possible to use a mixture of saturated aromatic hydrocarbons. For example, when a mixture of toluene (A) and methylcyclohexane (B) in a weight ratio of 1:1 is used, the average proportion of aromatic ring carbon number is calculated as follows:

$$\frac{\left(\frac{\text{Arom. Ring}\,CN\times\text{Wt.}}{\text{Mol. Wt.}}\right)_A + \left(\frac{\text{Arom. Ring}\,CN\times\text{Wt.}}{\text{Mol. Wt.}}\right)_B}{\left(\frac{\text{Total}\,CN\times\text{Wt.}}{\text{Mol. Wt.}}\right)_A + \left(\frac{\text{Total}\,CN\times\text{Wt.}}{\text{Mol. Wt.}}\right)_B} =$$

$$[(6\times 1/92)_A + (0\times 1/98)_B]/[(7\times 1/92)_A + (7\times 1/98)_B] = 0.44$$

The abbreviations in the above equation are as follows:

| | |
|---|---|
| Arom. Ring C N: | total number of aromatic carbons in a molecule |
| Wt. | weight |
| Mol. Wt. | molecular weight |
| Total C N | total number of carbons in a molecule |
| Subscript A | the above toluene (A) |
| Subscript B | the above cyclohexane (B) |

It will be noted that the average proportion of aromatic ring carbon numbers in this case is 44%, which is not suitable as saturated aromatic hydrocarbons used in the method of the present invention.

The fact that the average value of proportion of aromatic ring carbon number in one molecule of saturated aromatic hydrocarbon is less than 55%, means that the proportion of paraffinic carbon or naphthenic carbon is large. The use of such an aromatic hydrocarbon is not preferable because side reactions of decomposition and trans-alkylation occur vigorously.

By the way, the saturated aromatic hydrocarbon of 55% or more in average of the proportion of aromatic ring carbon number as a single compound or mixture is herein referred sometimes to "highly aromatic hydrocarbon".

When the aromatic compound used in the foregoing addition reaction is a highly aromatic hydrocarbon, it is possible to feed the aromatic compound for the reaction during the stopping of the feed of styrenic compound. For example, when styrene is added to xylene, the styrene is a raw material for addition reaction, at the same time, it is regarded as the above highly aromatic hydrocarbon, so that only the feed of styrene out of the feed of styrene and xylene, is stopped and the feed of xylene is continued with or without changing the feed rate as occasion demands.

In any case, when the highly aromatic hydrocarbon is fed into a reactor with stopping the feed of styrene, the inside of reactor must be maintained at a temperature higher by 5 to 150° C. than the reaction temperature in a liquid phase. In a reaction system, in which reaction temperature is varied with the passage of time, the above temperature must be higher by 5 to 150° C. than the highest temperature in the temperature variation. In many cases, because the reaction temperature is raised with the progress of reaction, the above highest temperature is generally set on the basis of the temperature just before the stopping of reaction.

When the temperature to feed the highly aromatic hydrocarbon into a reactor is lower than the above range, the feed of highly aromatic hydrocarbon must be continued for a long period of time, which causes the lowering of productivity. On the other hand, if the temperature is higher than the above range, it is not preferable because decomposition or trans-alkylation of highly aromatic hydrocarbon occurs vigorously.

It is necessary to maintain a liquid phase when the highly aromatic hydrocarbon is fed into a reactor, a pressure higher than autogenous pressure at its temperature is required. The pressure is generally in the range of 0.1 to 10 MPa. The time length to feed the highly aromatic hydrocarbon is not especially limited. It may be optionally selected from the range of 1 to 100 hours in view of productivity and effect.

Although the formation of unsaturated components is once increased in the reaction among styrene molecules, the undesirable reaction is suppressed after that by means of the above operation.

After the feeding of highly aromatic hydrocarbon, the feeding of reaction materials is commenced to restart the reaction. By the above operation, a fraction mainly containing an adduct of styrenic compound and aromatic compound having a bromine number that is reduced to the level before its increase, can be obtained. The bromine number is generally made 0.1 g/100 g or less, preferably 0.05 g/100 g or less.

When the bromine number is increased again, the reaction is stopped again and the highly aromatic hydrocarbon can be fed. This operation can be continued repeatedly until the effect of the present invention cannot be produced.

Furthermore, although it is possible to apply sintering or other treatment to the solid acid catalyst during these operation, such treatment is not especially required in general cases.

BEST METHOD FOR CARRYING OUT THE INVENTION

In the following, the present invention will be described in more detail with reference to examples.

EXAMPLE 1

A fixed-bed reactor installed in a thermostatic chamber was filled with 2 g of silica-alumina (trade name: IS-28, made by Mizusawa Industrial Chemicals, Ltd.). o-Xylene and styrene in a molar ratio of 10:1 were mixed together and the mixture was used as a raw material mixture.

To a reactor maintained at a temperature of 150° C. and a pressure of 1 MPa was fed 4 g/h in flow rate of the raw material mixture to carry out continuous aralkylation. Unreacted o-xylene and styrene were removed from reaction liquid by distillation to obtain a reaction product (a fraction mainly containing styrenated o-xylene). The bromine number of this reaction product was determined. The resultant values of bromine number from the start of reaction to 220 hours were in the range of 0.02 to 0.04 g/100 g.

After 275 hours, the bromine number was raised to 0.15 g/100 g. From this point, 4 g/h of o-xylene in place of the raw material mixture was fed to the reactor, which was maintained at a temperature of 190° C. and a pressure of 1 MPa and this operation was continued for 24 hours.

After that, aralkylation was restarted with feeding the raw material mixture and reaction mixture taken after 24 hours was analyzed. The result of bromine number was 0.03 g/100 g.

Industrial Applicability

In accordance with the method of the present invention, a fraction mainly containing a styrenic compound/aromatic compound adduct and low in bromine number can be obtained continuously without difficulty for a long period of time. This fraction of low bromine number is industrially valuable in the uses for solvents and so forth.

What is claimed is:

1. A method for producing a fraction of low bromine number mainly containing a styrenic compound/aromatic compound adduct, by feeding reaction materials of a styrenic compound and an aromatic compound having at least one hydrogen atom directly connected to the carbon atom of aromatic ring, to a fixed-bed flow reactor packed with a solid acid catalyst in a liquid phase at a temperature in the range of 40 to 350° C. to form a styrenic compound/aromatic compound adduct and obtaining a fraction mainly containing said adduct by distillation, wherein the feed of reaction materials to said reactor is stopped before the bromine number of said fraction increases up to 3 grams per 100 grams, after that, in place of the feed of said reaction materials, a saturated aromatic hydrocarbon having a mean value of the proportion of aromatic ring carbons relative to total carbons in a molecule of 55% or more is fed to said reactor in a liquid phase at a temperature higher by 5 to 150° C. than that of the reaction mixture just before the above stopping of feed of reaction materials, and then the feed of reaction materials is restarted to carry out the foregoing reaction so as to obtain a fraction of low bromine number.

2. A method of producing a low bromine number fraction as claimed in claim 1, wherein said aromatic compound is benzene, toluene, xylene, ethylbenzene, cumene or a mixture of them.

3. A method of producing a low bromine number fraction as claimed in claim 1, wherein said styrenic compound is styrene, α-methylstyrene or p-methyl-styrene.

4. A method of producing a low bromine number fraction as claimed in claim 2 wherein said styrenic compound is styrene, α-methylstyrene or p-methylstyrene.

5. A method for producing a low bromine number fraction as claimed in claim 1, wherein the bromine number of said fraction is 0.1 gram per 100 grams or less.

* * * * *